US012635944B2

(12) United States Patent
Fernandes Lopes et al.

(10) Patent No.: US 12,635,944 B2
(45) Date of Patent: May 26, 2026

(54) PORTABLE SYSTEM FOR PROGRESSIVE AEROBIC CARDIOVASCULAR ENDURANCE RUN TEST AND METHOD THEREOF

(71) Applicant: IPVC | Instituto Politécnico de Viana do Castelo, Viana do Castelo (PT)

(72) Inventors: Sérgio Ivan Fernandes Lopes, Viana do Castelo (PT); Luís Paulo Rodrigues, Melgaço (PT); João Miguel De Oliveira Passos, Viana do Castelo (PT); Filipe Clemente, Melgaço (PT); José Pedro Bezerra, Melgaço (PT); Pedro Miguel Do Vale Moreira, Viana do Castelo (PT)

(73) Assignee: IPVC | Instituto Politécnico de Viana do Castelo, Viana do Castelo (PT)

( * ) Notice: Subject to any disclaimer, the term of this patent is extended or adjusted under 35 U.S.C. 154(b) by 0 days.

(21) Appl. No.: 18/284,898

(22) PCT Filed: Nov. 29, 2022

(86) PCT No.: PCT/IB2022/061542
§ 371 (c)(1),
(2) Date: Sep. 29, 2023

(87) PCT Pub. No.: WO2023/119020
PCT Pub. Date: Jun. 29, 2023

(65) Prior Publication Data
US 2024/0180486 A1     Jun. 6, 2024

(30) Foreign Application Priority Data

Dec. 22, 2021     (PT) ........................................ 117663

(51) Int. Cl.
A61B 5/00     (2006.01)
A63B 71/06     (2006.01)
G16H 50/30     (2018.01)

(52) U.S. Cl.
CPC ........ *A61B 5/4884* (2013.01); *A63B 71/0622* (2013.01); *A63B 71/0686* (2013.01);
(Continued)

(58) Field of Classification Search
CPC .. A61B 5/4884; G16H 50/30; A63B 71/0622; A63B 71/0686; A63B 2225/74;
(Continued)

(56) References Cited

U.S. PATENT DOCUMENTS

| | | | | |
|---|---|---|---|---|
| 2012/0091921 A1* | 4/2012 | Buresta | ................. | A63B 69/12 |
| | | | | 315/320 |
| 2017/0259145 A1* | 9/2017 | Kline | ..................... | H05B 45/10 |
| 2019/0232138 A1 | 8/2019 | Bartels | | |

FOREIGN PATENT DOCUMENTS

| | | |
|---|---|---|
| CN | 105457250 | 4/2016 |
| CN | 211260430 | 8/2020 |

(Continued)

OTHER PUBLICATIONS

International Search Report and the Written Opinion Dated Feb. 24, 2023 From the International Searching Authority Re. Application No. PCT/IB2022/061542. (12 Pages).
(Continued)

*Primary Examiner* — Robert P Bullington

(57) ABSTRACT

A portable system and method for conducting a progressive aerobic cardiovascular endurance run test. The system having a strip with an interface configured for receiving input data from a user, sending instructions to a controller, and displaying data. The system further has a controller for processing instructions from the interface, controlling a
(Continued)

plurality of light emitters, and sending data to the interface. The system includes a variable length strip defining a length of the running path and connected to the controller comprising a plurality of light emitters for emitting a light signal to the subject. The input data includes the test parameters of the progressive aerobic cardiovascular endurance run test and the lap counts at each stage. The light signal is a light pattern that, at a pre-determined pace, changes a state of a light emitter in the sequence of the running direction.

18 Claims, 6 Drawing Sheets

(52) U.S. Cl.
    CPC ...... *G16H 50/30* (2018.01); *A63B 2071/0625* (2013.01); *A63B 2071/068* (2013.01); *A63B 2225/50* (2013.01); *A63B 2225/74* (2020.08); *A63B 2230/207* (2013.01)

(58) Field of Classification Search
    CPC ...... A63B 2071/0625; A63B 2071/068; A63B 2225/50; A63B 2230/207
    See application file for complete search history.

(56) References Cited

FOREIGN PATENT DOCUMENTS

| | | |
|---|---|---|
| GB | 2588997 | 5/2021 |
| WO | WO 2018/122010 | 7/2018 |
| WO | WO 2019/020482 | 1/2019 |
| WO | WO 2023/119020 | 6/2023 |

OTHER PUBLICATIONS

Beam Trainer "Beam Trainer", Beam Trainer App, 6 P., Jul. 16, 2014.

Bland et al. "Assessing Aerobic Fitness in Children: Comparison of Equations for Estimating Vo2max From the PACER Fitness Test", Medicine & Science in Sports & Exercise, 42(5): 546, #86, Jun. 3, 2010.

Cooper Institute "FitnessGram—PACER Test", GreenLight Fitness, Cooper Institute, 6 P.

Gao et al. "The Role of Ability Beliefs and Incentives in Middle School Students' Intention, Cardiovascular Fitness, and Effort", Journal of Teaching in Physical Education, 28(1): 3-20, Jan. 2009.

Gogol et al. "Interrater Reliability of Fitness Gram Test to Be Used as A Reliable Tool for Assessing Physical Fitness for School Children in Guwahati Urban Society of North-East India", International Journal of Research in Medical Sciences, 8(1):312-316, 2019.

Google Play "FitnessGram PACER: Ruval Enterprices", Apps on Google Play, 4 P., Updated Mar. 3, 2023.

Hussain et al. "Secure Seamless Bluetooth Low Energy Connection Migration for Unmodified IoT Devices", IEEE Transactions on Mobile Computer, 17(4): 927-944, Published Online Aug. 16, 2017.

Léger et al. "The Multistage 20 Metre Shuttle Run Test for Aerobic Fitness", Journal of Sports Sciences, 6(2): 93-101, Summer 1988.

Lightburne "Validation of the Progressive Aerobic Cardiovascular Endurance Run (PACER) Test for Children 7-13 Years Old", Medicine & Science in Sports & Exercise, 40(5): S463, #37, May 31, 2008.

Mahar et al. "Comparison of Aerobic Fitness Measured During Treadmill and PACER Tests: 2209", Medicine & Science in Sports & Exercise, 42(5): 546-547, May 2010.

Mahar et al. "Estimation of Aerobic Fitness From PACER Performance With and Without Body Mass Index", Measurement in Physical Education and Exercise Science, 22(3): 239-249, Published Online Jan. 24, 2018.

Mayorga-Vega et al. "Criterion-Related Validity of the 20-M Shuttle Run Test for Estimating Cardiorespiratory Fitness: A Meta-Analysis", Journal of Sports Science & Medicine, 14(3): 536-547, Aug. 11, 2015.

McClain et al. "Comparison of Two Versions of the PACER Aerobic Fitness Test", Journal of Physical Activity & Health, 3(S2): S47-S57, Apr. 2006.

Park et al. "Transmission of ECG Data With the Patch-Type ECG Sensor System Using Bluetooth Low Energy", 2013 International Conference on ICT Convergence, ICTC'13, Jeju Island, South Korea, Oct. 14-16, 2013, p. 289-294, Oct. 14, 2013.

Scott et al. "The Ability of the PACER to Elicit Peak Exercise Response in the Youth", Medicine & Science in Sports & Exercise, 45(6): 1139-1143, Jun. 2013.

Voss et al. "Does the Twenty Meter Shuttle-Run Test Elicit Maximal Effort in 11- to 16-Year-Olds?", Pediatric Exercise Science, 21(1): 55-62, Feb. 2009.

Youm et al. "RFID-Based Automatic Scoring System for Physical Fitness Testing", IEEE Systems Journal, 9(2): 326-334, Feb. 7, 2014.

* cited by examiner

PORTABLE SYSTEM FOR PROGRESSIVE AEROBIC CARDIOVASCULAR ENDURANCE RUN TEST AND METHOD THEREOF

RELATED APPLICATIONS

This application is a National Phase of PCT Patent Application No. PCT/IB2022/061542 having International filing date of Nov. 29, 2022, which claims the benefit of priority of Portugal Patent Application No. 117663 filed on Dec. 22, 2021. The contents of the above applications are all incorporated by reference as if fully set forth herein in their entirety.

FIELD AND BACKGROUND OF THE INVENTION

The present disclosure relates to a portable system for cardio-respiratory fitness assessment, for example, the Progressive Aerobic Cardiovascular Endurance Run (PACER) test, and method thereof.

Aerobic capacity tests are recurrently used to determine the maximum oxygen consumption, VO2max, of an individual. The VO2max expresses the maximum aerobic capacity and is considered the best cardio-respiratory fitness index.

A widely used test to estimate an athlete's aerobic capacity is the Progressive Aerobic Cardiovascular Endurance Run (PACER) test. This test consists of a shuttle race at a stage of 20 meters under a certain pace that increases in velocity every minute.

Regarding the validity and reliability of the results obtained in the PACER test for the maximum volume of oxygen, the authors in [1] concluded that the 20-meter version of the PACER test showed positive results in the above-mentioned criteria for both children and adults. The authors in [2] obtained identical results, with a slight difference in the results obtained in adults.

Regarding the testing of children, several studies [3] [4] [5] [6] [7] on young people and children have stated that the PACER test is a reliable way to evaluate maximum aerobic capacity, taking into consideration the effort made by them and the motivation to perform the test.

Regarding the PACER methods, in a school context, the space required for the test can be a conditioning factor. Authors in [8] concluded that both versions of the test (15 and 20 meters) provide similar results, recommending the 20-meter version.

When comparing the results obtained between a treadmill test and the PACER test, authors in [9] claim that the results were quite similar, although for young males there was a slight difference in the treadmill test.

When comparing the different equations used to obtain the maximum aerobic capacity, the authors in carried out a comparative study on four equations and concluded that all can be clinically used to estimate the maximum VO2 in children.

The authors in observed a minimal improvement in accuracy when adding the Body Mass Index (BMI) as a predictor, having concluded that the model with PACER and age as predictors has a high level of utility for fitness assessment of young people.

Regarding the implementation of physical tests, there are two main technologies used, radiofrequency identification (RFID) and Bluetooth Low Energy (BLE).

RFID is applied to sports, such as in marathons, soccer or even in gyms where a bracelet allows a device to read the athlete's identification and configure a specific test previously established, thus mitigating human error. The article is about a device that was developed to autonomously count laps during the PACER test. On this device, antennas are placed at the ends of the stage so that when the athlete reaches each one of them, a reader captures the identification of the athlete and checks if he/she complies with the established time.

BLE is a low power wireless technology that is widely used on the Internet of Things (IOT) ecosystem. The associated protocol is designed to allow networked devices to transmit bursts of data consuming a small amount of energy, allowing devices to operate under the power of a coin cell battery and run for an order of magnitude of years. Although this protocol has numerous advantages, when used for large data transmissions the low-power criterion tends to fade. Another important criterion to take into account is security, which, although the protocol itself already provides some protection measures, in a network of exposed sensors it may be not enough [13].

BLE can be deployed in several applications in the fitness field, such as devices for cardiorespiratory monitoring which use this protocol for personal area communications, enabling real-time data visualization in a mobile device. An example of this is the study done in [14], where the authors besides introducing, explaining, and comparing with the classic Bluetooth technology, also developed a prototype of heart rate monitoring in real-time.

The FitnessGram® PACER test is a program created by The Cooper Institute® to measure the maximum aerobic capacity of a student. It contains the audio that will guide students through the test, along with other resources such as scoresheets and instructions. All measurements have to be made manually and can be inserted later in a provided software. To implement the test, besides the audio CD that will create the auditory stimuli, other accessories are needed to delimit the test area.

During this test, some students may not have an effective perception of the pace that is imposed, especially when the test is performed in groups or in a noisy location, thereby impacting the obtained results.

The PACER for Schools [15]: PACER for Schools is a mobile application that can be acquired for free from an application store like Google PlayStore™. It allows the implementation of a PACER test using sound stimuli, also known as beeps. Also, it is possible to observe the elapsed time, imposed speed, distance travelled and the current level in the interface that has the application. However, it is configured so that just one student can run the test at a time, as the free version does not allow for use in groups. In the Pro version, there is the test functionality in groups, with the possibility to save and export the results individually and still visualize the comparison of the group in graphs. However, despite the mitigation of human error, this solution does not solve the problem of the lack of sense of the imposed pace.

The Beam Trainer Package contains a system of infra-red sensors that counts the passages in a very precise way and is accompanied by a mobile application. This system can be previously configured depending on the number of sensors used or the type of test to be implemented. Although it is configurable, this product was designed to be used mostly in sprint or round-trip tests. There is an option to implement the PACER test, where the human error is mitigated because the system contains the sensors that allow controlling the time. However, some issues remain to be solved such as the lack of awareness of the pace imposed, and it is only possible to perform the test individually because the product focuses on tests of speed and not resistance.

Moreover, these solutions rely solely on sound signals, excluding, thus, the possibility of the hearing-impaired to be tested independently.

When performed in a school context, having several young individuals performing the test at the same time, several other problems arise that may affect the reliability of the test such as: human errors in measurements and lap counting, lack of perception of the pace for the tested individual, and the difficulty in repeating the test indefinitely since it requires more than one test for the results to have the desired credibility.

Thus, there is a need for a multisensorial, robust, efficient, low cost, portable and less cumbersome implementation of aerobic tests that require a predefined pace.

These facts are disclosed in order to illustrate the technical problems addressed by the present disclosure.

SUMMARY OF THE INVENTION

The present disclosure relates to a portable system for fitness assessment, such as the progressive aerobic cardiovascular endurance run test of a subject, comprising: an interface configured for receiving input data from a user, sending instructions to a controller, and displaying data; a controller configured for receiving instructions from the interface, controlling a plurality of light emitters, and sending data to the interface; and, a variable length strip defining a length of the running path and connected to the controller comprising a plurality of light emitters for emitting a light signal to the subject. Wherein the input data are the test parameters of the progressive aerobic cardiovascular endurance run test and the lap counts at each stage. Wherein the light signal is a light pattern that, at a pre-determined pace, changes a state of a light emitter in the sequence of the running direction which defines the running pace to be met by the subject.

In an embodiment, the input data are the parameters of the progressive aerobic cardiovascular endurance run test are chosen from the following list: duration of the test, pre-determined pace to be met, number of subjects running, length of the test.

In an embodiment, the state of a light is one of the following: on/off state, light intensity, blinking frequency, colour of the light emitter, or a combination of these states.

In an embodiment, the variable length strip is rolled up in a coil.

In an embodiment, the variable length strip which comprises a plurality of light emitters is a strip of LED lights.

In an embodiment, a light signal is defined as about 1 meter of light-signalling LEDs which are, at the pre-determined pace and in the direction of running, temporarily and sequentially turned on.

In an embodiment, the interface is an electronic portable equipment such as: mobile phone, smartphone, tablet, laptop.

In an embodiment, the controller and the interface communicate via a wireless connection, preferably the Bluetooth Low Energy (BLE) protocol, or Wi-Fi if BLE is not available.

In an embodiment, the controller is a microcontroller unit with integrated Wi-Fi and BLE connectivity, preferably Espressif™ ESP32, ESP8266, Wemos® LOLIN D1 mini, or STMicroelectronics® STM32.

In an embodiment, the disclosed portable system further comprises a sound emitter, configured for receiving instructions from the controller and emitting an audio signal to the subject, for giving a starting sound test or warning the subject.

In an embodiment, the sound emitter comprises a loudspeaker, speaker, sound column, passive buzzer, powered by an audio amplifier, or a set of wirelessly connected headphones, headset, earphones, earbuds, or similar electronic equipment.

In an embodiment, the sound signal is a "Beep", an alarm, or a voice signal.

In an embodiment, the controller receives an instruction from more than one interface.

In an embodiment, the portable system emits a light signal or a light and a sound signal at the pre-determined pace and in the direction of running.

In an embodiment, the controller, and the sound and light emitters are powered via a battery, or a transformer connected to the power grid.

In an embodiment, the portable system further comprises a microphone configured to synchronize the start of the test when receiving an external sound signal such as a whistle, a clap, a starter pistol sound, or other starting sound.

Method of operation of the portable system to perform progressive an aerobic cardiovascular endurance run test of a subject comprising the steps: receiving the test parameters of the progressive aerobic cardiovascular endurance run test from a user in an interface and sending them to a controller; initializing the light emitters upon receiving said test parameters by said controller; receiving a start test instruction from a user in said interface and sending it to a controller; emitting a light signal pattern at an initial pre-determined pace, and increasing the pace of said light signal pattern at each stage according to said test parameters by controller; receiving lap counts of each subject being tested by a user in the interface, and giving a warning light when a subject fails to finish the stage for the first time; ending a subject test when fails to finish the stage for the second time; sending an end test instruction when the last subject fails to finish the stage for the second time from the interface to the controller; turning off the light emitters; calculating the maximum aerobic capacity of each subject.

Method of operation of the portable system, as described previously, comprising the steps: initializing the light emitters and sound emitters; emitting a sound signal upon receiving a start test instruction from a user; emitting an audio signal when a subject fails to finish the stage; turning off the light emitters and the sound emitters.

Method of operation of the portable system, as described previously, wherein the start test instruction is an external sound signal, such as a whistle, a clap, or a starter pistol sound, received by a microphone.

The progressive aerobic cardiovascular endurance run test is a 20-metre multi-stage run test that relies on an auditory stimulus to set a pace that increases the speed throughout each stage. When the subject fails to finish the stage, for the first time, before the sound signal, he/she is warned. For the second fail, the test ends for that subject.

It is possible to calculate the maximum aerobic capacity of the subject, along with other data such as age, height, weight, and gender, using the following equations [11]:

$$VO2\ Max = 3.46 \times (L + TL/(L \times 0.4325 + 7.0048)) + 12.2$$

$$VO2\ max = 31.714 + (TL \times 0.314);$$

$$VO2\ max = 44.862 + (TL \times 0.347) - (Age \times 1.050);$$

$$VO2\ max = 49.367 + (TL \times 0.331) - (Age \times 0.777) - (BMI \times 0.369)$$

where TL represents the total laps, L represents the level, and BMI represents the Body Mass Index.

The present disclosure has four main objectives: being low-cost, so that it can be easily acquired by any school or individual, portable, so that it can be used anywhere, reliable, so that measurements are accurate allowing to obtain credible results, and configurable, so that it not only performs the PACER test but also to be customized to other aerobic capacity exercises.

BRIEF DESCRIPTION OF THE SEVERAL VIEWS OF THE DRAWINGS

The following figures provide preferred embodiment for illustrating the disclosure and should not be seen as limiting the scope of the invention.

DESCRIPTION OF SPECIFIC EMBODIMENTS OF THE INVENTION

The present disclosure relates to a portable system comprising a sound and/or a light emitter that indicates to a subject the pace at which he/she must run to fulfil the stage within the established time. These emitters are controlled using an interface, e.g., a mobile application installed on a smartphone or tablet. A teacher or trainer configures the start and finish of the test, thus obtaining the results.

Figure 1:
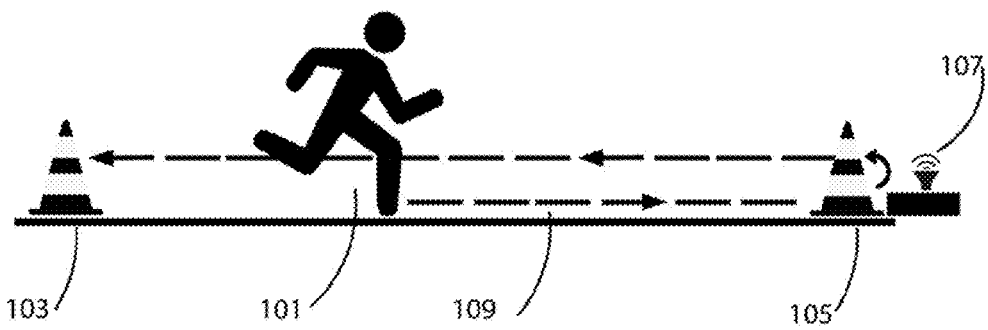
FIG. 1: Schematic representation of a classic PACER test implementation using a sound signal.

FIG. 1 shows a schematic representation of a classic PACER test implementation using a sound signal, where: 101 represents a subject that performs the test, 103 represents the 0-meter marker, 105 represents the 20-meter marker, 107 represents the sound signal, and 109 represents the testing track.

Figure 2:
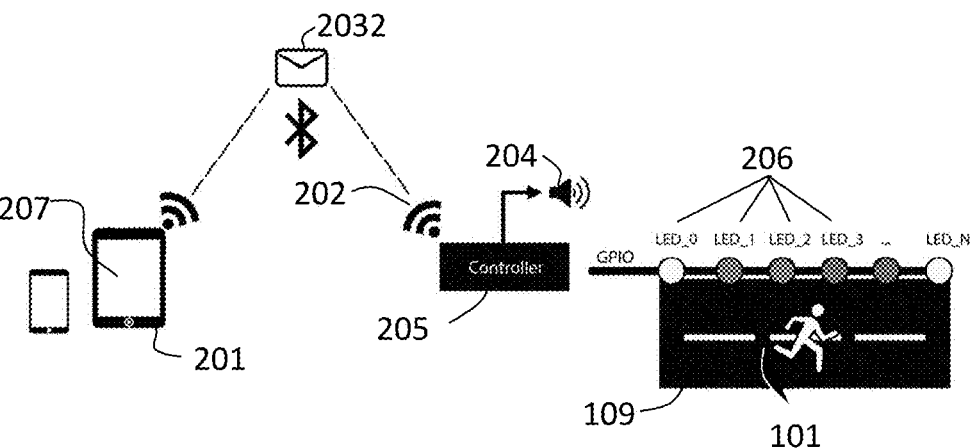
FIG. 2: Conceptual representation of an embodiment of the disclosed system with the respective sound and light signals.

FIG. 2 shows a conceptual representation of an embodiment of the disclosed system with the respective sound and light signals, where: 201 represents an interface, 202 represents a communication between the controller and the interface, 203 represents a message, 204 represents a sound emitter, 205 represents a controller, 206 represents a light emitter, 207 represents the mobile application interface, 101 represents a subject and 109 represents the testing track.

In an embodiment, the interface 201 is a peripheral input device with an operating system 207, such as a smartphone that runs a designed mobile application.

The designed mobile application is where a user can configure the parameters established for the test as well as enter some information, such as weight, age, etc. regarding a subject 101 who performs the test.

In an embodiment, the peripheral input device is one of the following: mobile phone, smartphone, tablet, laptop, or any other electronic portable equipment.

In an embodiment, the operating system 207 runs a mobile application designed for a smartphone or a tablet.

In one embodiment, the operating system 207 was designed to contain a mobile application in Android®, iOS®, or another operating system.

In an embodiment, the communication 202 between the interface 201 and the controller 205 is made via a wireless connection, preferably a Bluetooth Low Energy (BLE) protocol, or Wi-Fi if BLE is not available.

In an embodiment, the message 203 is a configuration message which is based on an ad hoc protocol and consists of instructions that the controller 205 is prepared to handle. This protocol defines the structure for the message transmitted by the BLE protocol, allowing a single message to send several parameters or instructions.

In an embodiment, the message 203 is a configuration message sent by the interface 201 to the controller 205 or data sent by the controller 205 to the interface 201.

In an embodiment, the controller 205 is chosen from a list: a microcontroller, Espressif™ ESP32, ESP8266, Wemos® LOLIN D1 mini, STMicroelectronics® STM32.

In an embodiment, the microcontroller comprises a 32-bit Xtensa LX6 dual-core processor, a clock frequency of 240 MHZ, 4 MB of flash memory, and 320 KB of RAM.

In an embodiment, the controller 205, upon receiving the data from the message 203, initializes the light 206 and sound 204 emitters for the test and waits until the user sets the initiation of the test.

In an embodiment, the controller 205 sends the test results to a cloud service.

In an embodiment, on the microcontroller development board there is a radio antenna for Bluetooth communications 202.

In an embodiment, the controller 205 acts as the controller for the output peripherals and hosts a Bluetooth server. It is capable to interpret the messages 203 received from the mobile application and act on the peripherals, as well as transmitting information to the operating system 207 with data regarding the test being performed.

In an embodiment, the light 206 and sound 204 emitters mark the progress of the test and/or give warnings. Providing, thus, information about the pace to the subject 101 during the test.

In an embodiment, the light emitter 206 is placed on the ground next to the running path.

In an embodiment, the light emitter 206 is placed in as a separator between the outward and return path.

In an embodiment, the light emitter 206 is chosen from the list: WS2812b RGB LED strip, WS2813 RGB LED strip, Adafruit NeoPixel RGB LED strip.

In an embodiment, the light emitter 206 comprises a LED strip with a density of 30 LEDs per meter, totalling 600 LEDs in the total of 20 meters.

In an embodiment, the sound emitter 204 reads the test instructions before stating to the subject 101.

In an embodiment, the sound emitter 204 is chosen from the list: loudspeaker, speaker, sound column, passive buzzer, piezo-tweeter.

In an embodiment, the sound emitter 204 comprises an individual and wirelessly connected headphones, headset, earphones, earbuds, or similar electronic equipment.

The testing track 109 of the test must be is flat and with adequate traction for running.

In an embodiment, the sound signal 107 is a "Beep" or a voice signal.

Figure 3:
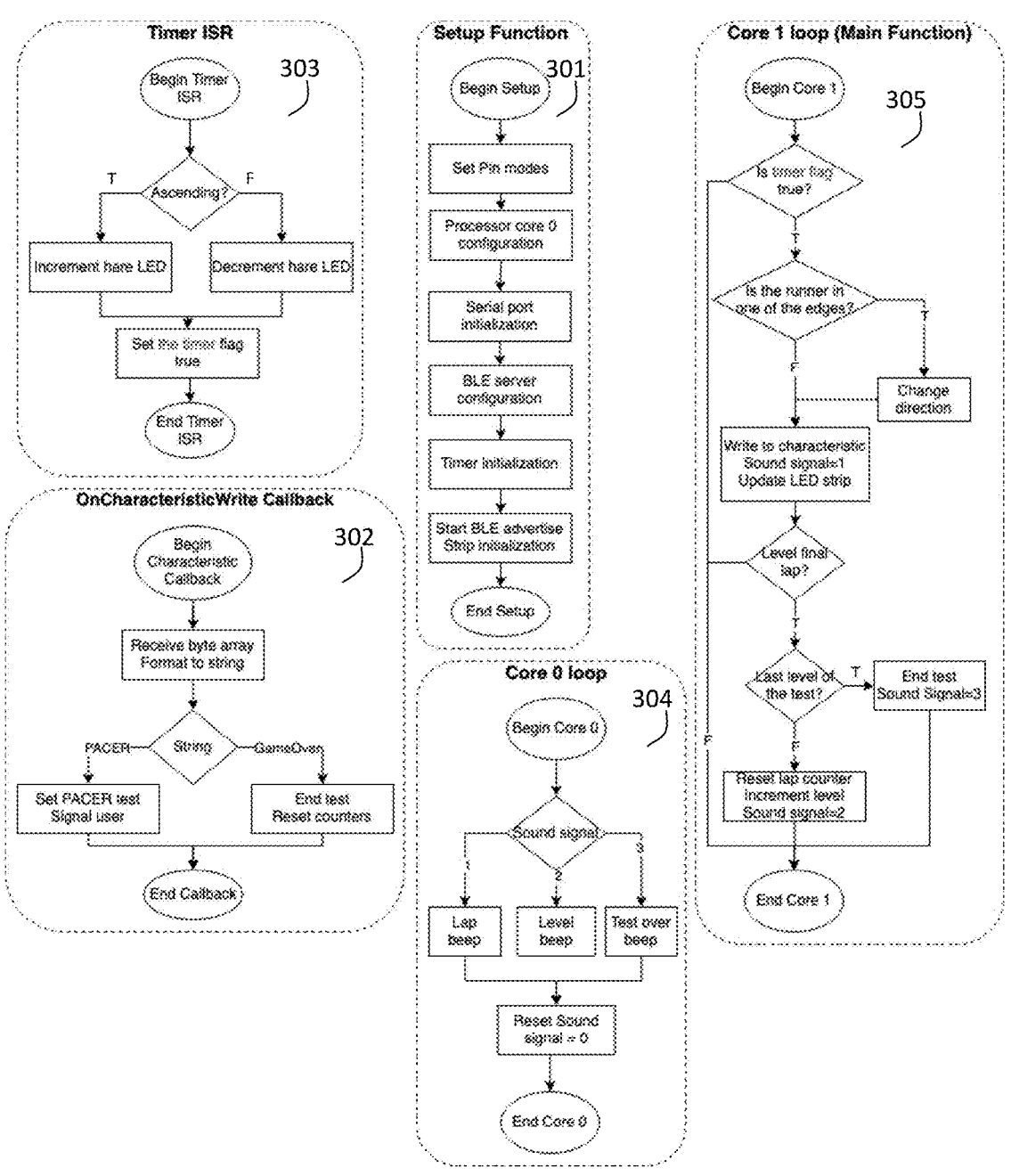
FIG. 3: Flowchart representing the method of implementation.

In an embodiment, FIG. 3 shows a flowchart representing the method of implementation, where 301 represents the block of the setup function, 302 represents the block of the characteristic write callback, 303 represents the block of the timer ISR (Interrupt Service Routine), 304 represents the core 0 loop, and 305 represents the block of the core 1 loop (main function).

The setup function 301 is the first block to be executed when the controller 205 is started. This block is executed only once when the controller 205 is started. At this stage, the setup function 301 performs the following steps: Set the pin modes; Configures the processor core 0; Initialization of the serial port; Configuration of the Bluetooth Low Energy (BLE) server; Initialization of the timer; Start BLE advertise and LED strip initialization.

In an embodiment, at the end of the setup function 301, the LED strip is initialized, which informs the user that the system is ready and listening for a sound signal, e.g., to a whistle blow, thus synchronizing the start of the test.

Once the execution of the setup function 301 is finished, the system does nothing until an instruction from the interface 201 is sent. The instruction sent is a string written by the mobile device in a GATT characteristic allocated in the BLE server running in 205.

When something is written to a GATT characteristic, the block of the characteristic write callback 302 is executed. The BLE server gets the payload, formats it and then a comparison between strings is made in order to execute the pretended task.

In an embodiment, one of the following tasks is performed: If the instruction wrote in the characteristic is "PACER": set the PACER test initial configuration; signal user; start test.

If the instruction wrote in the characteristic is "GameOver": terminate the running test; reset counters.

Whenever a timer is used in an MCU, it is necessary to set a tick rate. It is according to this tick rate that the timer will be triggered and with that, a flag is raised signalling the processor. The tick rate is defined by the lap time divided by the total number of LEDs on the strip. So, when this flag is raised, the timer ISR block 303 is executed.

This block is programmed to perform the following steps:
Increment or decrement the hare LED, depending on if the timer ISR is ascending.

The hare LED is the position on the strip that the athlete must keep up to finish the stage successfully. It starts in the position 0 m and goes until the last addressable LED on the strip.

Herein by "hare" is meant a sequence or pattern of light states that are changed according to a pre-defined pace.

In an embodiment, the core 0 loop 304 is a loop function set in the setup function 301. This function is programmed to emit one of three types of sound signal: lap beep (1), level beep (2), or test over beep (3), according to the core 1 loop 305.

In an embodiment, the core 1 loop (main function) 305 is a loop function of the controller 205. After the execution of setup function 301, the system repeats the execution of main function 305 indefinitely. Until the test starts, nothing happens in this function, but when the timer starts, a flag is raised every time it is triggered. This flag, represented as "timer flag" in the flowchart, allows the execution of a block responsible for some basic checks on the behaviour of the test, such as level and lap changes, LED strip manipulation, and sound signalling.

In an embodiment, this function may be programmed to:
Change direction if the runner is in one of the edges;

Write to characteristic, emit lap beep (1), and update LED strip if the runner is not in one of the edges or after change direction;

Reset lap counter, increment level and emit a level beep (2), if is in the level final lap and not on the last level of the test;

End the test if the timer flag is off, or if the runner is not on the level final lap, or if it is the last level of the test and emit a test over beep (3).

Figure 4A:
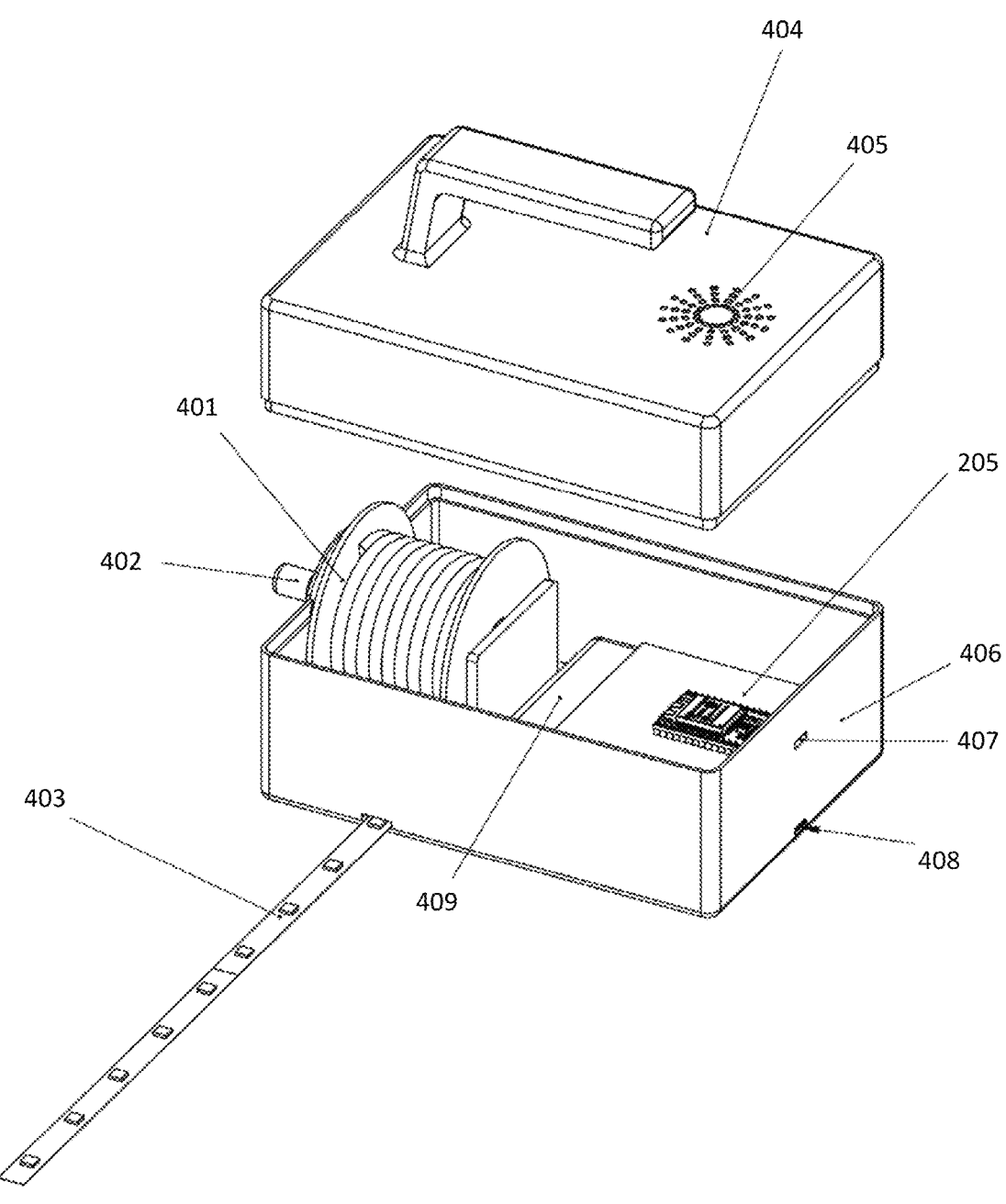
FIGS. 4A-4B: Schematic representation of an embodiment of a container comprising the disclosed system.
Figure 4B:
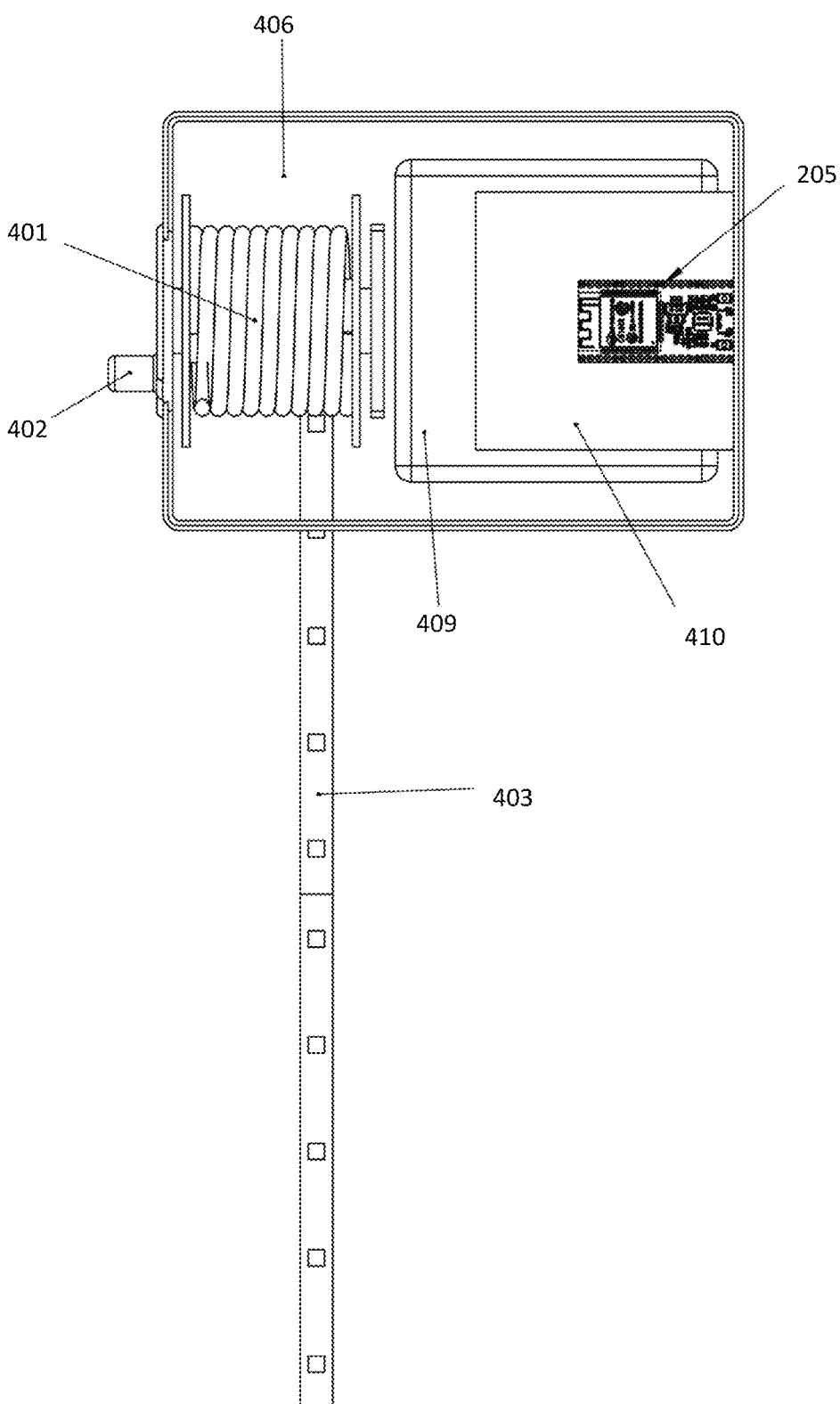

In an embodiment, FIG. 4A-4B shows a schematic representation of an embodiment of a container comprising the disclosed system, where 401 represents the LED strip coil, 402 represents the hand crank, 403 represents the LED strip, 404 represents the top part of the container, 405 represents the built-in loudspeaker, 406 represents the bottom part of the container, 407 represents the USB connector for the firmware update, 408 represents the battery charging port, 409 represents the battery, 410 represents the printed circuit board, and 205 represents a controller unit.

In an embodiment, all components have been assembled into an ELS® TK IP66 box.

Figure 5:
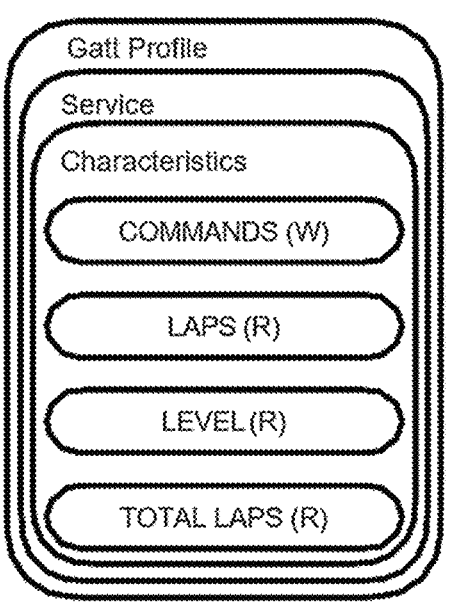
FIG. 5: Schematic representation of an embodiment of a Generic Attribute (GATT) profile belonging to the Bluetooth Low Energy (BLE) communications protocol with its service and characteristics.

In an embodiment, FIG. 5 shows a schematic representation of an embodiment of a GATT profile belonging to the BLE communications protocol with its service and characteristics.

In an embodiment, the communication 202 between the interface 201 and the controller 205 is done using the BLE protocol. By creating and configuring a BLE server on the controller 205, a peripheral device, such as a smartphone, can easily communicate with the controller 205 by writing in the characteristics defined for the service initialized. In this case, FIG. 5 shows the GATT profile with the service defined and its characteristics. Each characteristic can have different properties: read (R), write (W), notify, or indicate. A peripheral device can only write to characteristics that have the write property and read from those who have the read property.

In an embodiment, four characteristics are used, namely, one for sending instructions to the controller 205 and the other three for storing the information needed to obtain results. The first characteristic is named "Commands", it has the writing property since this feature is only to place instructions for the controller 205 to interpret. The remaining characteristics are named "Laps", "Level", and "Total Laps". They have the read property because it is through these that an operating system 207, such as a mobile application, gets data from the test to obtain the test results.

Figure 6:
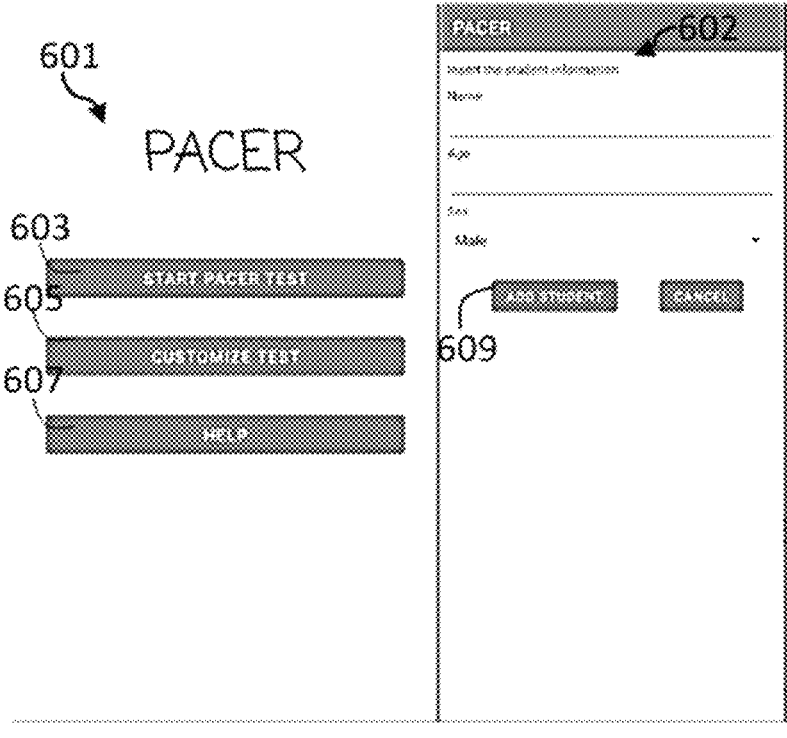
FIG. 6: Schematic representation of an embodiment of a mobile application layout.
Figure 6:
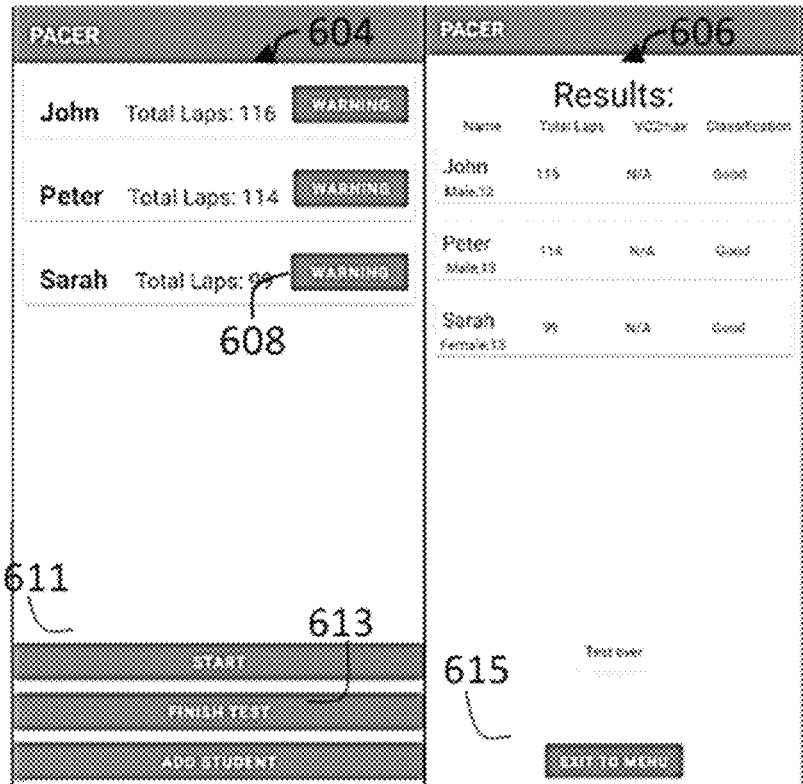

In an embodiment, FIG. 6 shows a schematic representation of an embodiment of a mobile application layout, where 601 represents the screen layout of the initial menu, 602 represents the screen layout of the student insertion activity, 604 represents the screen layout of the test control activity, 606 represents the screen layout of the test results activity, 603 represents a "Start Pacer Test" button, 605 represents a "Customize Test" button, 607 represents a "Help" button, 608 represents a "Warning" button, 609 represents a "Add Student" button, 611 represents a "Start" Button, 613 represents a "Finish Test" button, and 615 represents a "Exit to Menu" button.

In an embodiment, after selecting the PACER test 603 from the initial menu 601, the test control activity 604 is displayed. Initially, there are no students entered for running the test, and therefore it is needed to press the "Add Students" button 609.

When you press the button 609 the student insertion activity 602 is displayed. Here you can fill in some information about the student required for calculating the results.

As the test proceeds, to assign a warning or even to end the test for a student, the "Warning" button 608 is pressed. When it is first pressed, a warning is displayed on the screen signalling the user that the warning has been given. The second time, the total number of laps already taken is saved in order to calculate results.

When the test is over for all the students or whenever the user intends to end the test, pressing the "Finish Test" button 613 closes the control activity 604 and displays test results activity 606.

In an embodiment, the test results activity 606 shows the results for each of the students.

In an embodiment, if the age of the subject 101 is over 17, the maximum aerobic capacity is calculated, and a rating is assigned based on the average performance for the age.

In an embodiment, if the age of the subject 101 is under 17, only the rating is assigned.

In an embodiment, the light emitter 206 is mounted into a flexible strip.

In an embodiment, the light emitter 206 is rolled up, e.g., for easier storage or transportation.

In an embodiment, the microcontroller 205 is configured to be ready to execute the test after setting of the parameters of the test.

In an embodiment, the general operation method comprises the following steps: Set the parameters of the test; Enter the subjects 101 data, e.g., age and gender; Put the controller 205 in standby mode.

After the insertion, the microcontroller is, waiting for the application signal. When signalled, the microcontroller starts the output peripherals, i.e., the sound 204 and light 206 emitters, according to the test settings for each level or stage.

In an embodiment, the sound emitter 204, using a sound signal, announces the end of the stage, an increase in the imposed speed or the end of the test.

In an embodiment, the light emitter 206, using a light signal, displays the pace to be met during each stage. For example, by switching on each of the lights according to where the athlete should be in order to finish the stage, and thus, remain on the test.

In an embodiment, during the test, a maximum of 30 LEDs out of 600 LEDs, corresponding to about 1 meter of light signalling, are turned on simultaneously.

In an embodiment, the process of shortening the time in between stages is repeated until the subject 101 is not able to finish the stage successfully for the second time or by indication of the mobile application. After the test is over, the application queries the characteristic values for computing results that are later displayed on the test results activity 606.

In an embodiment, the disclosed system has the following advantages: performing a PACER test; customizing a test; Automation of results; Exporting results to spreadsheet; Grouping students/subjects to facilitate re-testing In an embodiment, the Bluetooth server that acts as the communications center for the operating system 207 is also created and the characteristics that store the information configured.

In another embodiment, the test is fully customizable.

In an embodiment, the controller 205, the sound 204 and light 206 emitters are powered via a battery, or a transformer connected to the power grid.

In an embodiment, the controller 205, the sound 204 and light 206 emitters are powered by an AC/DC 5V 8A transformer.

In an embodiment, the present disclosure has found that, for PACER tests, it presents:

reliable and accurate results in measuring the maximum aerobic capacity of a subject using the following equations:

$$VO2\ Max=3.46 \times (L+TL/(L \times 0.4325+7.0048))+12.2$$

$$VO2\ max=31.714+(TL \times 0.314);$$

$$VO2\ max=44.862+(TL \times 0.347)-(Age \times 1.050);$$

$$VO2\ max=49.367+(TL \times 0.331)-(Age \times 0.777)-(BMI \times 0.369)$$

where TL represents the total laps, L represents the level and BMI represents the Body Mass Index.

it is suitable for application to a young audience, namely children and adolescents, since, besides a sound signalization, there is a programmed LED light strip lying next to the place where they are running;

it can be deployed in different spaces, since both the 15-meter and 20-meter versions present identical results;

with the disclosed interface 201 it is easier to repeat the test on the same group of athletes and to later analyse the results obtained.

It is to be appreciated that certain embodiments of the disclosure as described herein may be incorporated as code (e.g., a software algorithm or program) residing in firmware and/or on a computer useable medium having control logic for enabling execution on a computer system having a computer processor, such as any of the servers described herein. Such a computer system typically includes memory storage configured to provide output from execution of the code, which configures a processor in accordance with the execution.

The disclosure can be realized by way of a general-purpose computer processor or a purpose-specific computer processor like a microcontroller, on a purpose-specific card or module, embedded in a circuit or chip, such as a custom-built chip, an FPGA (field-programmable gate array) or FPGA-like chip, or as a firmware program recorded in media such as ROM, EPROM, or the like. Examples include general purpose hardware like Atmel™ based Arduino™ devices, Intel™ based devices, ARM™ based devices, or custom purpose systems like a custom-built SoC (system on a chip), namely as a semiconductor intellectual property core (SIP core), IP core, or IP block (reusable unit of logic, cell, or integrated circuit layout to be used in a chip manufacture).

Examples of controllers include, for example, ESP-32, depending on the application or the required performance.

The code can be arranged as firmware or software, and can be organized as a set of modules, including the various modules and algorithms described herein, such as discrete code modules, function calls, procedure calls or objects in an object-oriented programming environment. If implemented using modules, the code can comprise a single module or a plurality of modules that operate in cooperation with one another to configure the machine in which it is executed to perform the associated functions, as described herein.

The term "comprising" whenever used in this document is intended to indicate the presence of stated features, integers, steps, components, but not to preclude the presence or addition of one or more other features, integers, steps, components, or groups thereof. The disclosure should not be seen in any way restricted to the embodiments described, and a person with ordinary skill in the art will foresee many possibilities to modifications thereof. The above-described embodiments are combinable. The following claims further set out particular embodiments of the disclosure.

REFERENCES

[1] L. A. Léger, D. Mercier, C. Gadoury, and J. Lambert, "The multistage 20 metre shuttle run test for aerobic fitness," Journal of Sports Sciences, vol. 6, no. 2, pp. 93-101, 1988, PMID: 3184250. DOI: 10.1080/02640418808729800. eprint: https://doi.org/10.1080/02640418808729800. [On-line]. Available: https://doi.org/10.1080/02640418808729800.

[2] Mayorga-Vega, D. A.-S. P., and V. J., "Criterion—related validity of the 20-m shuttle run test for estimating cardiorespiratory fitness: A meta-analysis.," Journal of sports science—& medicine, vol. 14, no. 3, pp. 536-547, 2015. [Online]. Avail-able: https://www.ncbi.nlm.nih.gov/pmc/articles/PMC4541117/.

[3] D. J. J., C. Sarah, P. Kyle, F. Clifton, and B. R. FACSM, "The ability of the pacer test to measure aerobic capacity of prepubescent boys and girls," Medicine—& Science in Sports—& Exercise, vol. 47, no. 5S, pp. 230-231, 2015. DOI: 10.1249/01.mss.0000477055.53373.7b.

[4] C. Voss and G. Sandercock, "Does the twenty meter shuttle-run test elicit maximal effort in 11- to 16-year-olds?" Pediatric Exercise Science, vol. 21, no. 1, pp. 55-62, 2009. [Online]. Available: https://journals.humankinetics.com/view/journals/pes/21/1/article-p55.xml.

[5] P. Gogoi and N. Bhattacharyya, "Interrater re-liability of fitness gram test to be used as a reliable tool for assessing physical fitness for school children in Guwahati urban society of north-east India," International Journal of Research in Medical Sciences, vol. 8, no. 1, pp. 312-316, 2019, ISSN: 2320-6012. DOI: 10.18203/2320-6012.ijrms20195928. [Online]. Available: https://www.msjonline.org/index.php/ijrms/article/view/7519.

[6] Z. Gao, K. R. Lodewyk, and T. Zhang, "The role of ability beliefs and incentives in middle school students' intention, cardiovascular fitness, and effort," Journal of Teaching in Physical Education, vol. 28, no. 1, pp. 3-20, 2009. [Online]. Available: https://journals.humankinetics.com/view/journals/jtpe/28/1/article-p3.xml.

[7] T. J. Lightburne, "Validation of the progressive aerobic cardiovascular endurance run (pacer) test for children 7-13 years old," Medicine—& Science in Sports—& Exercise, vol. 40, no. 5, S463, 2008. [Online]. Available: https://journals.lww.com/acsm-msse/Fulltext/2008/05001/Validation of the Progressive Aerobic.2632.aspx.

[8] J. J. McClain, G. J. Welk, M. Ihmels, and J. Schaben, "Comparison of two versions of the pacer aerobic fitness test," Journal of Physical Activity —& Health, vol. 3, no. s2, S47-S57, 2006. [On-line]. Available: https://journals.humankinetics.com/view/journals/jpah/3/s2/article-pS47.xml.

[9] M. M. T., A. M. Guerieri, M. S. Hanna, and C. D. Kemble, "Comparison of aerobic fitness measured during treadmill and pacer tests: 2209," Medicine—& Science in Sports—& Exercise, vol. 42, no. 5, pp. 546-547, 2010. DOI: 10.1249/01.MSS.0000385346.79194.9a. [Online]. Available: https://journals.lww.com/acsm-msse/Fulltext/2010/05001/Comparison of Aerobic Fitness Measured during.1617.aspx.

[10] B. J. R., E. Joey, P. K. FACSM, C. Joe, Y. Kimbo, and S. Darijan, "Assessing aerobic fitness in children: Comparison of equations for estimating vo2max from the pacer fitness test," Medicine—& Science in Sports —& Exercise, vol. 42, no. 5, p. 546, 2010. DOI: 10.1249/01.MSS.0000385344.02066.15.

[11] M. T. Mahar, G. J. Welk, and D. A. Rowe, "Estimation of aerobic fitness from pacer performance with and without body mass index," Measurement in Physical Education and Exercise Science, vol. 22, no. 3, pp. 239-249, 2018. DOI: 10.1080/1091367X.2018.1427590.eprint: https://doi.org/10.1080/1091367X.2018.1427590. [Online]. Available: https://doi.org/10.1080/1091367X.2018.1427590.

[12] S. Youm, Y. Jeon, S. Park, and W. Zhu, "RFID-based automatic scoring system for physical fitness testing," IEEE Systems Journal, vol. 9, no. 2, pp. 326-334, 2015. DOI: 10.1109/JSYST.2013.2279570.

[13] S. R. Hussain, S. Mehnaz, S. Nirjon, and E. Bertino, "Secure seamless Bluetooth low energy connection migration for unmodified IoT devices," IEEE Transactions on Mobile Computing, vol. 17, no. 4, pp. 927-944, 2018. DOI: 10.1109/TMC. 2017.2739742.

[14] Young-jin Park and Hui-sup Cho, "Transmission of ECG data with the patch-type ECG sensor system using Bluetooth low energy," in 2013 International Conference on ICT Convergence (ICTC), 2013, pp. 289-294. DOI: 10.1109/ICTC.2013.6675359.

[15] Fitnessgram pacer apps on Google PlayStore™. [On-line]. Available: https://play.google.com/store/apps/details?id=rudy.android.pacer&hl=enUS&gl=US.

[16] Beam trainer—beam trainer app. [Online]. Available: https://www.beamtrainer.com/.

[17] Pacer test—Fitnessgram by the Cooper Institute. [Online]. Available: https://www.fitnessgram.net/pacertest/.

The invention claimed is:

1. Portable system for the progressive aerobic cardiovascular endurance run test of a subject, comprising:
    an interface configured for receiving input data from a user, sending instructions to a controller, and displaying data;
    a controller configured for receiving instructions from the interface, controlling a plurality of light emitters, and sending data to the interface; and,
    a variable length strip defining a length of the running path and connected to the controller comprising a plurality of light emitters for emitting a light signal to the subject; wherein the variable length strip is rolled up in a coil;
    a microphone configured to synchronize a start of the test of the subject when receiving an external sound signal;
    wherein the input data comprises test parameters of the progressive aerobic cardiovascular endurance run test and lap counts at each stage,
    wherein the light signal having a light pattern that, at a pre-determined pace, changes a state of a light emitter in a variable length strip unrolled from the coil in the sequence of the running direction;
    wherein the test parameters are chosen from group consisting of a duration of the test, a pre-determined pace to be met, a number of subjects running, and a length of the test.

2. Portable system according to the previous claim 1 wherein the state of a light is one of the following: on/off state, light intensity, blinking frequency, colour of the light emitter, or a combination of these states.

3. Portable system according to the previous claim 1 wherein the variable length strip which comprises a plurality of light emitters is a strip of light emitting diode (LED) lights.

4. Portable system according to the previous claim 3 wherein a light signal is defined as about 1 meter of light-signaling light emitting diodes (LEDS) which are, at the pre-determined pace and in the direction of running, temporarily and sequentially turned on.

5. Portable system according to the previous claim 1 wherein the interface is an electronic portable equipment such as: mobile phone, smartphone, tablet, laptop.

6. Portable system according to the previous claim 1 wherein the controller and the interface communicate via a wireless connection, preferably the Bluetooth Low Energy (BLE) protocol, or Wi-Fi if BLE is not available.

7. Portable system according to the previous claim 1 wherein the controller is a microcontroller unit with integrated Wi-Fi and BLE connectivity.

8. Portable system according to the previous claim 1 further comprising a sound emitter configured for receiving instructions from the controller and emitting an audio signal to the subject.

9. Portable system according to the previous claim 8 wherein the sound emitter comprises a loudspeaker, speaker, sound column, passive buzzer, piezo-tweeter, or a set of wirelessly connected headphones, headset, earphones, earbuds, or similar electronic equipment.

10. Portable system according to the previous claim 8 wherein an audio signal is a "Beep", an alarm, or a voice signal.

11. Portable system according to the previous claim 1 wherein the controller receives an instruction from more than one interface.

12. Method of operation of a portable system for perform progressive an aerobic cardiovascular endurance run test of a subject, wherein the portable system, comprising:

an interface configured for receiving input data from a user, sending instructions to a controller, and displaying data;

a controller configured for receiving instructions from the interface, controlling a plurality of light emitters, and sending data to the interface; and, a variable length strip defining a length of the running path and connected to the controller comprising a plurality of light emitters for emitting a light signal to the subject; wherein the variable length strip is rolled up in a coil;

a microphone configured to synchronize a start of the test of the subject when receiving an external sound signal;

wherein the input data comprises test parameters of the progressive aerobic cardiovascular endurance run test and lap counts at each stage, wherein the light signal having a light pattern that, at a pre-determined pace, changes a state of a light emitter in a variable length strip unrolled from the coil in the sequence of the running direction;

wherein the test parameters are chosen from a group consisting of a duration of the test, a pre-determined pace to be met, a number of subjects running, and a length of the test;

wherein the method comprising:

receiving the test parameters of the progressive aerobic cardiovascular endurance run test from a user in an interface and sending them to a controller;

initializing the light emitters upon receiving said test parameters by said controller;

receiving a start test instruction from a user in said interface and sending it to a controller;

emitting a light signal pattern at an initial pre-determined pace, and increasing the pace of said light signal pattern at each stage according to said test parameters by controller;

receiving lap counts of each subject being tested by a user in the interface, and giving a warning light when a subject fails to finish the stage for the first time;

ending a subject test when fails to finish the stage for the second time;

sending an end test instruction when the last subject fails to finish the stage for the second time from the interface to the controller;

turning off the light emitters; and calculating the maximum aerobic capacity of each subject.

13. Method of operation of the portable system according to the previous claim 12 comprising:

initializing the light emitters and sound emitters;

emitting a sound signal upon receiving a start test instruction from a user;

emitting an audio signal when a subject fails to finish the stage;

turning off the light emitters and the sound emitters.

14. Method of operation of the portable system according to the previous claim 12 wherein the start test instruction is an external sound signal, such as a whistle, a clap, or a starter pistol sound, received by a microphone.

15. Computer readable non-transitory medium program comprising instructions, which when the program is executed by a computer, causes the computer to perform the method of the claim 12.

16. Computer-readable non-transitory medium being stored therein the computer program of the previous claim.

17. The portable system according to claim 1, wherein the controller is configured to activate only light emitters positioned in the unrolled portion of the variable length strip while maintaining light emitters in the rolled portion of the coil in a deactivated state during operation of the test.

18. The portable system according to claim 1, wherein during the test, the controller activates a maximum of 30 light emitters simultaneously out of a total of 600 light emitters in the variable length strip, wherein the activated light emitters correspond to approximately one meter of light signaling in the unrolled portion.

* * * * *